United States Patent [19]

Greenbaum

[11] Patent Number: 4,789,436
[45] Date of Patent: Dec. 6, 1988

[54] METHOD AND APPARATUS FOR NONDESTRUCTIVE IN VIVO MEASUREMENT OF PHOTOSYNTHESIS

[75] Inventor: Elias Greenbaum, Oak Ridge, Tenn.

[73] Assignee: The United States of America as represented by the United States Department of Energy, Washington, D.C.

[21] Appl. No.: 158,500

[22] Filed: Feb. 22, 1988

[51] Int. Cl.$^4$ .................... G01N 27/30; G01N 27/54
[52] U.S. Cl. ................................. 204/1 T; 204/403; 204/415; 435/29
[58] Field of Search .................. 204/415, 1 P, 403; 435/29

[56] References Cited

U.S. PATENT DOCUMENTS 2,913,386 11/1959 Clark, Jr. ........................ 204/195 P
4,076,596 2/1978 Connery et al. .................. 204/1 T
4,576,705 3/1986 Kondo et al. ..................... 204/406

OTHER PUBLICATIONS

Delieu et al., New Phytol. 89:165–178 (1981), "Polarographic Measurement of Photosynthetic Oxygen Evolution by Leaf Discs".
Phelan et al., American Lab., Jul. 1982:65–72, "A Maintenance-Free Dissolved Oxygen Monitor".
Friese, J. Electroanal. Chem. 106:409–412 (1980), "A New Type of Clark Oxygen Electrode".
Ley et al., Biochimica et Biophysica Acta. 680:95–106 (1982), "Absolute Absorption Cross-Sections for Photosystem II and the Minimum Quantum Requirement for Photosynthesis in Chlorella Vulgaris".
Hale et al., J. Electroanal. Chem., 107:281–294 (1980), "Some Considerations of the Steady-State and Transient Behavior of Membrane-Covered Dissolved Oxygen Detectors".

Primary Examiner—G. L. Kaplan
Attorney, Agent, or Firm—Stephen D. Hamel; Judson R. Hightower

[57] ABSTRACT

A device for in situ, nondestructive measurement of photosynthesis in live plants and photosynthetic microorganisms is disclosed which comprises a Clark-type oxygen electrode having a substantially transparent cathode comprised of an optical fiber having a metallic grid microetched onto its front face and sides, an anode, a substantially transparent electrolyte film, and a substantially transparent oxygen permeable membrane. The device is designed to be placed in direct contact with a photosynthetic portion of a living plant, and nondestructive, noninvasive measurement of photosynthetic oxygen production from the plant can be taken by passing light through the fiber-optic cathode, transparent electroyte and transparent membrane, and onto the plant so that photosynthesis occurs. The oxygen thus produced by the plant is measured polargraphically by the electrode. The present invention allows for rapid, nondestructive measurements of photosynthesis in living plants in a manner heretofore impossible using prior art methods.

7 Claims, 2 Drawing Sheets

METHOD AND APPARATUS FOR NONDESTRUCTIVE IN VIVO MEASUREMENT OF PHOTOSYNTHESIS

FIELD OF THE INVENTION

The invention relates to a Clark-type oxygen electrode having a cathode comprised of a fiber optic member having a metallic grid etched thereto which can make noninvasive measurements of photosynthesis in living organisms.

BACKGROUND OF THE INVENTION

The interest in obtaining rapid and accurate measurements of photosynthesis in plants and photosynthetic microorganisms has grown considerably with the recent upswing in environmental monitoring and pollution control. In particular, field and agricultural photosynthetic productivity have been examined in terms of how extensively various pollutants, such as acid rain or toxic chemicals, have affected the environment. It is of considerable value to be able to quickly and accurately assess photosynthesis in the field via instruments or methods which are safe and which do not themselves adversely affect the plant life.

The key parameter in any study of environmental effects on photosynthetic activity is the evolved oxygen from the plants. It is well established in this area that the proteins and enzymes associated with light-activated water splitting and oxygen evolution are among the most fragile components of the photosynthetic apparatus. It therefore follows that a careful study of plant oxygen production can serve as an important warning tool in early detection of adverse effects on plants and other organisms caused by environmental pollutants.

One commonly used tool in assessing levels of evolved oxygen is known as a Clark-type oxygen electrode. This electrode, as further described in U.S. Pat. No. 2,913,286 (Clark,Jr.), basically consists of an electrolytic cell having a cathode, an anode, and an electrolytic medium between the two, and is used to polarographically measure the amount of certain substances, such as oxygen, in a solution. The electrolytic medium, however, is separated from the solution to be measured by a selectively permeable membrane barrier, which allows the substance that one desires to measure to enter the electrolyte and thus be measured apart from the compounds in the test solution.

There are many Clark-type oxygen electrodes currently in use, some of which are used to polarographically monitor the evolution of oxygen by plants. One such device is described in Delieu et al., *New Phytol*, 89:165 (1981), and consists primarily of an electrode chamber employing a Clark-type electrode which is used to assess oxygen production from a circular disc sectioned from a leaf. This device requires the use of a sectioned leaf and thus cannot be used to measure photosynthesis in live leaves. Additionally, this chamber requires an electrolyte solution and an external light source which is projected through the roof of the chamber in order to impinge upon the photosynthetic material.

Other Clark-type oxygen electrodes have been described previously, including U.S. Pat. No. 4,076,596 (Connery et al.), wherein an electrolytic cell for measuring oxygen in a fluid is disclosed having a first and second electrode. Additionally, Phelan et al., *Amber. Lab*, July 1982, pp. 6514-72, disclose a Clark-type probe for measuring dissolved oxygen in polluted water samples for use in determining biological oxygen demand, and Friese, J. Electronal. Chem. 106:409 (1980) discloses a Clark electrode which is characterized by a thin layer of ground glass coated with polytetraflourethylene which replaces the membrane barrier. Still other articles are known which disclose use of Clark electrodes in assessing oxygen production, such as Ley et al., *Biochimica et Biophysica Acta*, 680:95 (1982) and Hale et al., *J. Electroanal Chem.* 107:281 (1980).

Most of these prior art devices in this area are cumbersome or complex, and are often designated for lab experiments only. None of the presently known Clark-type oxygen electrodes can be used to rapidly and noninvasively take an accurate measure of photosynthetic oxygen production in the field using a live plant source. What is desired, therefore, is to provide a noninvasive, nondestructive device and method to measure in situ photosynthesis rapidly and accurately using live plants.

SUMMARY OF THE INVENTION

According to the present invention, there is provided a device for in situ, nondestructive measurement of photosynthesis in live plants and photosynthetic microorganisms which comprises a Clark-type oxygen electrode having a semitransparent cathode made of an optical fiber with a metallic grid microetched into its sides and front face, an anode, a substantially transparent electrolyte film and a substantially transparent oxygen permeable membrane. The device is designed to be placed in direct contact with the leaf or other photosynthetic system to be measured, and a measurement of photosynthetic oxygen production is taken by conducting light through the optical fiber cathode, electrolyte film and membrane so that it impinges upon the photosynthetic material, causing oxygen to be produced which is then polarographically measured by the electrode. The method and apparatus of the present invention improves upon the prior art by providing a system by which plant photosynthesis can be monitored in the field rapidly and accurately, yet noninvasively and nondestructively as well.

BRIEF DESCRIPTION OF THE DRAWING FIGURES

DETAILED DESCRIPTION OF THE PREFERRED EMBODIMENTS

Figure 1:
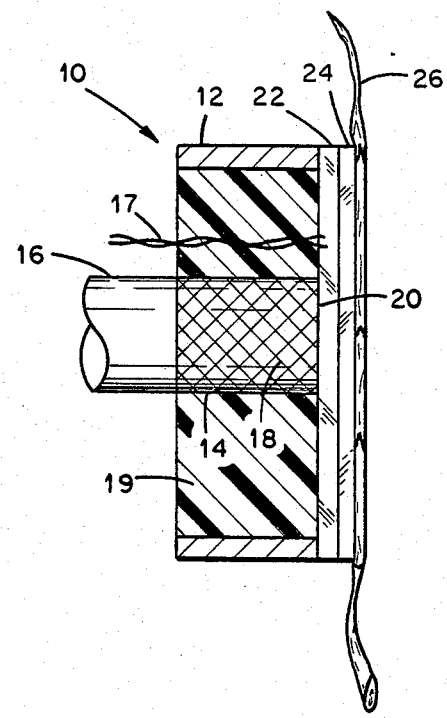
FIG. 1 is a side view of the electrode of the present invention.
Figure 2:
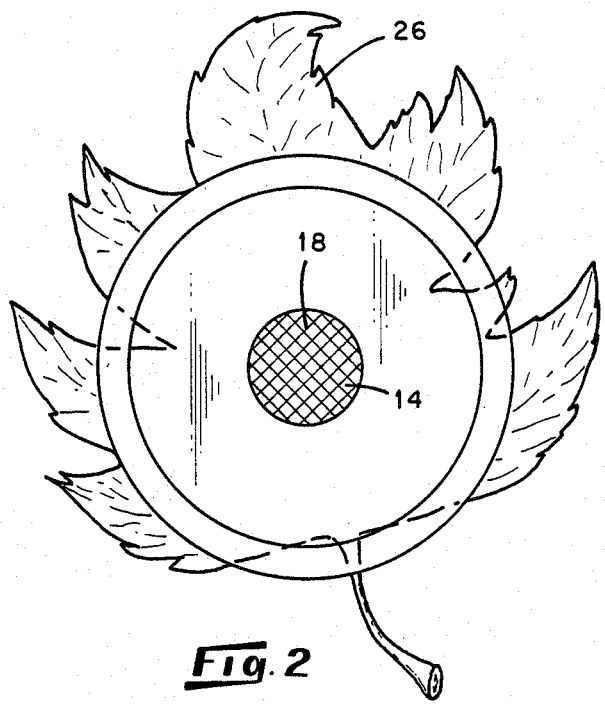
FIG. 2 is a top view of FIG. 1.

According to the present invention, and as best observed in FIGS. 1 and 2, there is provided a device 10 for the nondestructive measurement of photosynthesis in living organisms comprising a Clark-type oxygen electrode 12 having a substantially transparent cathode 14 comprised of an optically transparent member 16, preferably made from a fiber-optic material, which has a metallic grid 18 on its side and front face 20. In contact with front face 20 of cathode 14 is a substantially transparent electrolyte film 22, and in contact with the electrolyte film is a substantially transparent oxygen permeable membrane 24. The oxygen permeable membrane 24 is designed to be placed next to or directly in contact with a photosynthetic system to be measured, such as a leaf 26 from a live plant, so that when light is directed onto the leaf, oxygen photosynthetically produced in response to the light will diffuse through the membrane 24 and be measured polarographically by the electrode 12. The electrode 12 further includes a conventional anode 17, preferably made of silver or silver chloride, which is in contact with the electrolyte film 22.

Figure 3:
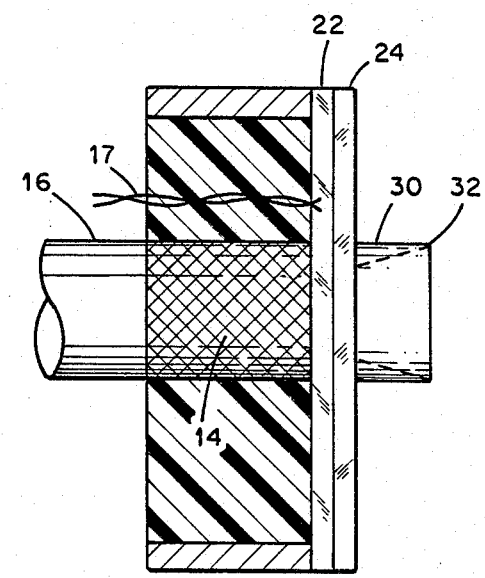
FIG. 3 is a side view of another embodiment of the present invention.

The cathode 14 of the present invention is preferably comprised of a cylindrical optical fiber 16, having a metallic grid 18 microetched on its front face and sides, as indicated by the cross-hatching observed in FIGS. 1-3. It is preferred that the metallic grid be comprised of platinum, although other conductive metals conventionally used in this type of electrode, such as gold, may be employed. The quantity of platinum that is deposited onto the optical fiber should be such that the surface at which light emerges is substantially clear. The microetching should continue around the body of the fiber such that electrical continuity is maintained for establishing electrical contact with an external circuit. The cathode can be sized to take measurements of any desired leaf, but an optical fiber of from about one-half inch to one inch in diameter is appropriate for most leaves. When the surface to be measured is smaller, as in, e.g., a blade of grass, smaller microetched optical fibers may be used.

The substantially transparent electrolyte film 22 used in the present invention is preferably a thin transparent layer of a metallic chloride salt, such as potassium chloride or sodium chloride. The oxygen permeable membrane 24 should be comprised of a thin transparent sheet which is permeable to oxygen gas, but impermeable to water or KCl ions. Examples of suitable oxygen barriers for the present invention would be cellophane or a thin sheet of silicone rubber.

The Clark-type electrode 12 of the present invention also preferably comprises an insulating support stem 19 which surrounds the anode 17 and the cathode 14, and is cocentric with the cathode. The stem 19 acts to add support to the electrode so that the apparatus can be readily placed on a leaf or other appropriate photosynthesic plant surface. The support stem is preferably comprised of an opaque machinable plastic which effectively blocks off outside light impinging upon the plant, so that the only light reaching the leaf will be provided by the fiber optic cathode. This allows one to make a standard measurement of photosynthesis regardless of the background light present. The insulating support stem can be made of any suitable opaque plastic such as Lucite, Plexiglass, Teflon, etc.

In operation, the electrode of the present invention is used to measure photosynthesis of a living plant by first positioning it next to a living photosynthetic organism so that the oxygen produced by the organism in response to light provided by the cathode will diffuse through the oxygen permeable membrane. If it is a broad leaf plant that is to be monitored, the membrane 24 of the electrode 12 is pressed flush against the leaf surface 26 in a noninvasive and nondestructive manner. The membrane surface 25 which is placed in contact with the leaf can be appropriately contoured to best cover a particular leaf's geometry. With the electrode in place, a beam of light is caused to be passed through the optical fiber 16, and this light passes out the front face 20 of cathode 14, through transparent electrolyte film 22, and oxygen permeable membrane 24 so as to impinge upon the surface of the leaf. When the light falls on the leaf, oxygen is produced by the plant photosynthetically, and this oxygen production is detected polarographically by diffusion back through the oxygen permeable membrane 24 to the microetched platinum cathode 14.

The electrode of the present invention can be moved to a variety of positions on the leaf surface for monitoring oxygen evolution from different portions of the leaf. Two independent optical fiber light pipes and cathodes can be used to provide differential measurements. For instance, one light fiber-cathode combination can serve as a reference and the other can be the working system. An example of the reference could be a dark control, a constant steady-state light level, a modulated light level, or monochromatic light source.

The polarographic oxygen assays possible through use the device of the present invention can also be modified so as to incorporate a multiplicity of light fibers and platinum cathodes, each to be operated independently. For example, an array of 100 electrodes can be constructed in which each light fiber has its own light source and platinum microetched cathode, but with all electrodes electrically communicating with the analytical equipment through a common electrolyte film and anode. In this way, oxygen evolution from 100 different locations on the leaf surface can be measured simultaneously, thereto enabling a "contour map" of the photosynthetic capacity of the leaf's surface to be determined. The output of the array of electrodes can be interfaced to a microcomputer and automatic data processing acquisition system in order to further provide for processing and analysis of the gathered information.

Another embodiment of the device of the present invention can be observed in FIG. 3. This embodiment includes a retaining cup 30 projecting from and attached to the transparent oxygen permeable barrier 24. The retaining cup 30, having a relatively sharp edge 32, is positioned directly in front of the fiber-optic cathode 14, and is used for rapidly measuring photosynthetic activity of single colonies of algae or other photosynthetic microorganisms growing on a solid growth medium, such as an agar block (not shown). The dimensions of the retaining cup are suitably chosen so that a single algal colony can be isolated and retained within the cup by pressing the sharp edge perpendicularly against the plane defined by the solid agar surface. The colony will thus be trapped within a volume defined by the agar surface, the oxygen permeable membrane, and the walls of the retaining cup, and photosynthetic oxygen production from the colony can be measured polarographically by the electrode of the present invention after the colony is illuminated by light coming from the fiber-optic cathode. By moving the probe from colony to colony over the surface of the agar, each colony can be separately encased and rapidly assayed for photosynthetic activity. The use of the retaining cup with the present electrode thus allows for the convenient and accurate measurement of photosynthetic capabilities of many different colonies of oxygen-producing microorganisms.

The electrode described in the above embodiments should be calibrated before measurements are taken using known amounts of the gases to be measured. Absolute calibration is possible by replacing the leaf or retaining cup with a chamber hermetically sealed to the oxygen permeable membrane that communicates with the cathode by gaseous diffusion. Preferably, the chamber will incorporate an area larger than the surface area of the microetched cathode. By changing the partial pressure of the gases in the chamber, either with calibrated gas mixtures or physical pressure changes, it is possible to correlate the polarographic current with the absolute partial pressure to which the cathode is exposed. Once calibrated, it is then possible to use the electrode of the present invention to safely and conveniently take nondestructive measurements of oxygen production in living photosynthetic organisms.

Figure 4A:
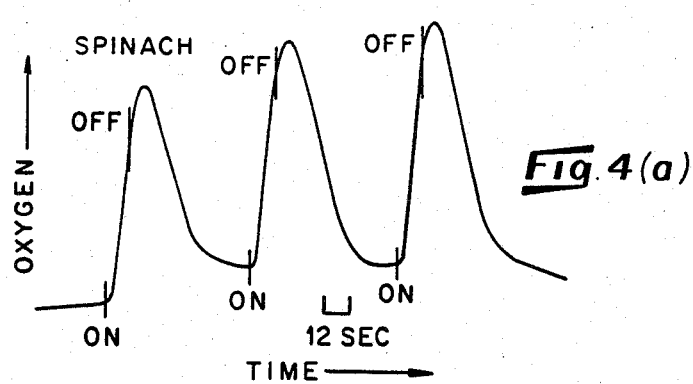
FIGS. 4a–4c are graphic representations of polarographic measurements of evolved oxygen taken using a prototype of the present invention.
Figure 4B:
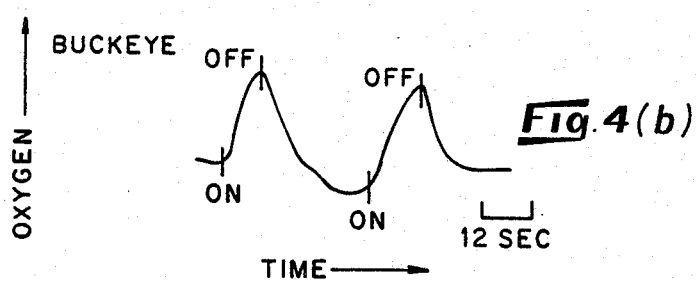
Figure 4C:
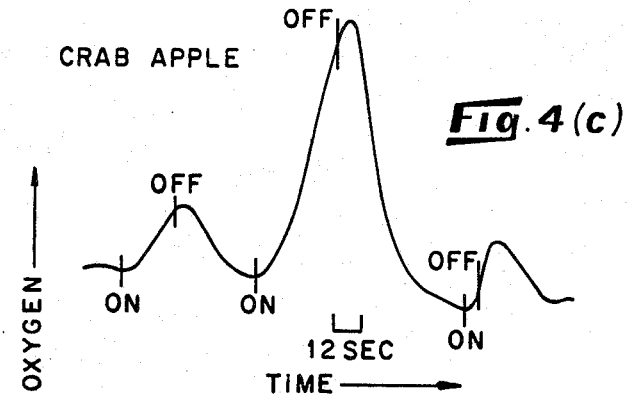

A prototype of an instrument employing the basic idea of the present invention has been constructed, and has been tested on several varieties of leaves. Although this prototype does not utilize a microetched semitransparent platinum cathode, its dimensions are comparable to the present invention. Polarographic tracings from various leaves taken using the prototype are presented in FIGS. 4a–4c. These tracings were taken from the indicated plants by pressing the leaves flush against the membrane of a Clark-type electrode with a clear glass plate. The leaves were then irradiated with the collimated beam of a helium-neon laser. The laser beam first passed through the glass plate and then impinged on the portion of the leaf adjacent to the platinum cathode. The polarographic recordings of FIGS. 4a–4c correspond to the oxygen evolved in the plant leaf indicated over the time period of the tests. These tests show the feasibility of using the apparatus of the present invention for safely and noninvasively measuring the photosynthesis response of living plants.

What is claimed is:

1. A device for nondestructive measurement of photosynthesis in living organisms comprising:
   a Clark-type oxygen electrode having a substantially transparent cathode comprised of an optically transparent member having a metallic grid on its sides and front face, an anode, a substantially transparent electrolyte film in contact with the front face of said cathode, and a substantially transparent oxygen permeable membrane in contact with said electrolyte film, so that the oxygen produced by the photosynthetic system of a living photosynthetic organism in response to light directed onto said organism from said cathode will diffuse through said membrane and said electrolyte film so as to be measurable polarographically by said Clark-type oxygen electrode.

2. A device according to claim 1 wherein said optically transparent member is comprised of a fiber-optic material.

3. A device according to claim 2 wherein said optically transparent member is a cylindrical optical fiber.

4. A device according to claim 1 wherein said metallic grid is comprised of platinum.

5. A device according to claim 1 wherein said metallic grid is comprised of gold.

6. A device according to claim 1 further comprising a retaining cup attached to said oxygen permeable membrane to allow measurement of photosynthesis in photosynthetic microorganisms.

7. A method of nondestructively measuring photosynthesis in living organisms which comprises the steps of:
   (a) positioning a Clark-type oxygen electrode having a substantially transparent cathode comprised of an optically transparent member with a metallic grid on its sides and front face, a substantially transparent electrolyte film in contact with the cathode, and a substantially transparent oxygen permeable membrane next to a living photosynthetic organism so that oxygen produced by the organism in response to light will diffuse through the oxygen permeable membrane;
   (b) causing light to be conducted through the optically transparent member of the cathode so that the light travels through the electrolyte film and oxygen permeable membrane and impinges upon the photosynthetic organism so that oxygen is produced by the organism; and
   (c) measuring polargraphically the oxygen produced by the photosynthetic organism.

* * * * *